United States Patent
Barak

(10) Patent No.: US 6,478,973 B1
(45) Date of Patent: *Nov. 12, 2002

(54) PROCESS FOR THE DISINFECTION OF WATERS

(75) Inventor: Ayala Barak, Jerusalem (IL)

(73) Assignee: Dead Sea Bromine Group, Beer Sheva (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/023,984

(22) Filed: Feb. 13, 1998

Related U.S. Application Data

(63) Continuation of application No. 08/639,708, filed on Apr. 29, 1996, now abandoned, which is a continuation of application No. 08/272,276, filed on Jul. 8, 1994, now abandoned, which is a continuation of application No. 07/892,533, filed on Jun. 1, 1992, now abandoned.

(30) Foreign Application Priority Data

Jun. 3, 1991 (IL) .................................. 98352

(51) Int. Cl.$^7$ .................................................. C02F 1/50
(52) U.S. Cl. ...................................... 210/756; 210/764
(58) Field of Search ................................ 210/754, 756, 210/764; 422/37

(56) References Cited

U.S. PATENT DOCUMENTS

| | | | | |
|---|---|---|---|---|
| 4,431,729 A | * | 2/1984 | Falxa | 430/569 |
| 4,566,986 A | * | 1/1986 | Waldmann | 252/175 |
| 4,767,564 A | * | 8/1988 | Kitchens et al. | 252/187.26 |
| 4,872,999 A | * | 10/1989 | Schild et al. | 210/754 |

FOREIGN PATENT DOCUMENTS

JP 56-13512 3/1981

* cited by examiner

*Primary Examiner*—Ivars Cintins
(74) *Attorney, Agent, or Firm*—Dechert

(57) ABSTRACT

A process for killing microorganisms and controlling biofouling in high chlorine demand waters comprises mixing two components, one of which is an oxidant and the other an ammonium salt, and adding the mixture immediately to the aqueous system to be treated.

8 Claims, No Drawings

PROCESS FOR THE DISINFECTION OF WATERS

This is a continuation of U.S. Ser. No. 08/639,708 filed Apr. 29, 1996 now abandoned, which is a continuation of U.S. Ser. No. 08/272,276 filed Jul. 8, 1994 now abandoned, which is a continuation of U.S. Ser. No. 07/892,533 filed Jun. 1, 1992 now abandoned.

BACKGROUND OF THE INVENTION

Biological fouling of circulating water is a known and well documented problem. Several factors contribute to the problem and govern its extent: water temperature; water pH; organic and inorganic nutrients either from air drawn into the system or from materials naturally occurring in the water or continuously supplied during plant operation; aerobic/anaerobic conditions; the presence/absence of sunlight, etc.

Algae, fungi, bacteria, as well as other simple life forms are found in circulating water. The types of microorganisms and the extent of microbial growth depend on the water source and on the other factors.

Biological growth in circulating water can foul pipelines, accelerate corrosion, attack wood, decrease heat transfer, plug filters, cause imperfections in paper sheets; decompose sizing mixtures, and cause many other process interferences.

Oxidizing biocides including chlorine gas, hypochlorous acid, bromine and other oxidizing biocides are widely used in recirculating water.

"Chlorine demand" is defined as the quantity of chlorine that is reduced or otherwise transformed to inert forms of chlorine by substances in the water; and standard methods have been established for measuring it. In this specification and claims "chlorine demand" is as measured by procedures outlined in "Standard Methods for the examination of water and waste water,", 16th edition, Methods §409, pages 316–319. The methods are based on applying a specific dose of chlorine to the medium and measuring the residual chlorine left after a given contact time. Chlorine-consuming substances include ammonia and amino derivatives; sulfides, cyanides, oxidizable cations, pulp lignins, starch, sugars, oil, water treatment additives like scale and corrosion inhibitors.

Microbial growth in the water and in biofilms contribute to the chlorine demand of the water and to the chlorine demand of the system to be treated. Oxidizing biocides were found to be ineffective in waters containing a high chlorine demand, including heavy slimes. Non-oxidizing biocides are usually recommended for such waters.

Chlorination of water having a high content of ammonia or other ammino-derivatives results in the formation of chloramines. Chloramines are described as poor biocides relative to hypochlorous or hypobromous acid. According to literature, chloramines are slow to react and may be more persistent in water systems (The NALCO water handbook, 1988, PCT/US 89/02730 21.6.1989, Great Lakes Chem. Corp. Wat. Sci. Tech. 20 No 11/12, pp. 385–39, 1988, by M. D. Sobsey et al., National Academy of Science, 1980, Drinking Water and Health, Vol. 2, National Academy Press, Washington, D.C.).

Chloramination of drinking water occurs when chlorine reacts with small amounts of ammonia either present in or added to the water.

Traditional chloramination occurs with the addition of free chlorine to the total amount of water for reaction with small amounts of ammonia present in the water, or added to the water in known amounts. Only one reference describes the use of pre-formed monochloramine for the post-disinfection of drinking water (J. Beck et al., Aqua I, 25–33, 1986). In this work, chloramines were formed by mixing ammonium sulfate and hypochlorite solution at a concentration of 1000 ppm; pH was adjusted to 7.5 before the point of dosage to avoid carbonate precipitation.

Chloramines were used to control aftergrowth and biofouling in the surface seawater reverse osmosis plants (Desalination 74, 51–67 (1989) and European Patent Application No. 90108872.4,11.05.90, for Du Pont de Nemours and Company). This patent claims the use of chloramine to inhibit regrowth following dechlorination in liquid process streams containing chlorine degradable organic material, that when in degraded form provides energy and carbon source that is assimilable by microorganisms. The chloramine for the process was made in situ by adding $NH_3$ gas, $NH_4OH$, $NH_4Cl$ or $(NH_4)_2SO_4$. The sources of chlorine were $Cl_2$ gas, NaOCl, $Ca(OCl)_2$ and electrolytically generated chlorine.

Chloramines formed in situ during chlorination of cooling water containing ammonia, is considered to have no biocidal effect in the treatment of cooling towers, since chloramines are quickly stripped due to their high volatility [G. Holz Warth et al., Water Res. 18(1), 1421–1427 (1984)].

The disinfection of highly turbid waste water using chlorine had improved when ammonia was added to the waste water (in situ), when longer contact times were allowed Atasi Khalil Z. et al.; Proc. Annu. Conf. Am. Water Works Assoc., 1988 (Pt. 2), pp. 1763–1770).

Ammonium bromide was not mentioned as a possible source for chloramines. The usual sources are ammonia, ammonium chloride and ammonium sulfate.

Its is a purpose of the invention to provide a process and compositions for killing microorganisms and inhibiting biofouling in waters, especially in cooling waters and aqueous systems having a high chlorine demand waters, and more especially in cooling waters and aqueous systems having a high chlorine demand.

It is another purpose of the invention to provide such a process and compositions that have a high biocidal effect and a high initial rate of kill in high chlorine demand waters.

It is further purpose of the invention to provide such a process and compositions the biocidal effect and the properties of which are constant and predetermined.

Other purposes and advantages of the invention will become apparent as the description proceeds.

SUMMARY OF THE INVENTION

The process according to the invention comprises mixing two components, one of which is an oxidant, preferably an active chlorine donor and still more preferably sodium hypochlorite, and the other, an ammonium salt, preferably chosen among halides, sulfates and nitrates, and adding the biocidal concentrate immediately to the aqueous system to be treated. The frequency, duration and concentration should be determined in each individual case so as to be sufficient to control biofouling.

Preferably, the two ingredients are mixed in a specific order, and specifically the oxidant is added to a solution of the ammonium salt. In a preferred form of the invention, the oxidant is NaOCl and is slowly added to a well-mixed solution of the ammonium salt diluted in the range of 0.01% to 2% equimolar to chlorine, preferably until a final concentration of chlorine in the mixture has reached 0.01–1% as chlorine. Either batch or continuous formation of the biocidal stock solution is effective.

The biocidal mixture was found to be more effective than other oxidizing biocides (such as chlorine or bromine) whenever the demand in the water system exceeds 1.8 ppm $Cl_2$ out of 2.0 ppm $Cl_2$ within 60 minutes. The percentages of ingredients are given as weight percent.

The mole ratio N/Cl is preferably 1:1. An excess of N may be used.

The temperature of the water to which the mixture is added, can be in the region of 10–60° C. The temperature of the solution of ammonium salt should be 10–30° C. when NAOCl is added. The pH is controlled by the concentration of the NAOCl solution; preferably the pH range should be 8.0–12.5. The active ingredient was effective at pH 7 and at pH 8. Some decrease in efficacy was noted at pH 9.

The frequency and duration of treatment and concentrations of active ingredient needed in order to maintain good control of biofouling should be determined in each individual case. However, good control was achieved at a level of 3 mg/l as chlorine (4.2 kg $NH_4Br$ for 1000 m$^3$).

The biocidal mixture is very effective for shock treatment of fouled systems, even in cases where the water demand is low, and enables the effective daily use of oxidizing biocides. A level of 9 mg/l (as chlorine) is sufficient to clean a fouled system.

In preferred forms of the invention, the mixture is formed and fed either batchwise or continuously by any suitable means, such as by a liquid metering pump or by gravity.

The invention comprises the solutions prepared as described above.

DETAILED DESCRIPTION OF PREFERRED EMBODIMENTS

The following are non-limitative examples of possible applications of the process:

Recirculating cool water
Brewery pasteurizer
Air washer
Evaporative cooling water
Scrubbers
Pond and lagoon water
Closed water-cooling systems
Food plant disinfection
Bleaching—pulp and paper etc.

The process according to the invention is compatible with other water treatment chemicals, corrosion and scale inhibitors, etc.

EXAMPLE 1

Efficacy in Buffer at pH-7.5 Against Pseudomonas,

Dosage: 1 ppm as $Cl_2$;

Chlorine demand: 0.1 ppm out of 1 ppm within 20 minutes $NH_4Br+NaOCl$: stock concentration: 1000 ppm as $Cl_2$ Preparation of stock solution: $NH_4Br$ was dissolved in de-ionized water (2761 ppm). NaOCl (2000 ppm as $Cl_2$) was quickly added dropwise to the ammonium bromide solution while stirring the mixture. The stock solution was used immediately.

TABLE I

|  | Survivors (cfu/ml) after time (minutes) | | | |
| --- | --- | --- | --- | --- |
| Biocide | 1 | 5 | 10 | 20 |
| NaOCl | $4 \times 10^6$ | $1 \times 10^5$ | $4 \times 10^2$ | 0 |
| NaOCl + NaBr (1:1) | $5 \times 10^3$ | $4 \times 10^2$ | $4 \times 10$ | 0 |
| $NH_4Br$ + NaOCl (1:1) | $6 \times 10^6$ | $2 \times 10^6$ | $5 \times 10^3$ | 0 |
| Control | — | — | — | $9 \times 10^6$ |

Results in Table I indicate higher rates of kill for NaOBr and NaOCl as compared to $NH_4Br+NaOCl$ in water with low demand for chlorine.

EXAMPLE 2

Efficacy of Ammonium Bromide at Various pHs

Examined MO: bacillus mycoides

Dose: 2 ppm as $Cl_2$ $NH_4Br+NaOCl$: molar ratio 1:1; stock concentration: 0.5%; $NH_4Br+NaOCl$ was either pre-mixed or added in situ to the buffer.

Demand: 1.8 ppm out of 2 ppm of $Cl_2$ within 60 minutes.

TABLE II

|  | Survivors: cfu/ml | | | | | | | | |
| --- | --- | --- | --- | --- | --- | --- | --- | --- | --- |
|  | pH — 7.0 | | | pH — 8.0 | | | pH — 9.0 | | |
| Treatment | 60 m | 180 m | 24 h | 60 m | 180 m | 24 h | 60 m | 180 m | 24 h |
| $NH_4Br$ + NaOCl premix | $7 \times 10^4$ | $2 \times 10^4$ | $2 \times 10^2$ | $2 \times 10^5$ | $9 \times 10^4$ | $2 \times 10^2$ | $1 \times 10^5$ | $9 \times 10^4$ | $1 \times 10^4$ |
| $NH_4Br$ + NaOCl in situ | $2 \times 10^5$ | $6 \times 10^4$ | $2 \times 10^4$ | $1 \times 10^5$ | $7 \times 10^4$ | $1 \times 10^4$ | $2 \times 10^5$ | $1 \times 10^5$ | $1 \times 10^5$ |
| NaOCl | $1 \times 10^5$ | $1 \times 10^5$ | $1 \times 10^5$ | $3 \times 10^5$ | $1 \times 10^5$ | $1 \times 10^5$ | $1 \times 10^5$ | $1 \times 10^5$ | $1 \times 10^5$ |
| NaOCl + NaBr 1:1 | $2 \times 10^5$ | $1 \times 10^5$ | $1 \times 10^5$ | $3 \times 10^5$ | $2 \times 10^5$ | $2 \times 10^5$ | $2 \times 10^5$ | $1 \times 10^5$ | $1 \times 10^5$ |
| non-treated | — | $3 \times 10^6$ | $5 \times 10^5$ | $3 \times 10^6$ | — | $1 \times 10^5$ | $5 \times 10^5$ | — | $4 \times 10^5$ |

Table II shows that pre-mixed ($NH_4Br+NaOCl$) a higher rate of kill as compared to either NaOCl or NaOBr, as the demand for chlorine increases. Efficacy was slightly impaired at pH from 8.0 to 9.0.

EXAMPLE 3

Efficacy of $NH_4C+NaOCl$ in Water Taken from a Citrus Juice Evaporator: Comparison to Non-Oxidizing Biocides Water demand: higher than 30 ppm of $Cl_2$ (out of 30 ppm $Cl_2$) within 60 minutes.

Concentration of stock solution ($NH_4Cl+NaOCl$): 1000 ppm.

Algicol II is a quaternary ammonium salt.

TABLE III

| Biocide | dose mg/l | Survivors (cfu/ml) after time (hours) | | |
|---|---|---|---|---|
| | | 1 | 24 | 7 days |
| Kathon | 30 | $2 \times 10^6$ | $7 \times 10^2$ | $7 \times 10^2$ |
| MBT | 30 | $1 \times 10^6$ | $1 \times 10^3$ | $8 \times 10^2$ |
| Algicol II | 100 | $5 \times 10^6$ | $4 \times 10^6$ | $9 \times 10^6$ |
| $NH_4Cl$ + NaOCl | 30 | 0 | 0 | 0 |
| Control | — | $6 \times 10^6$ | $3 \times 10^7$ | $1 \times 10^7$ |

Results in Table III indicate that a mixture of $NH_4Cl+NaOCl$ was more effective than 3 non-oxidizing biocides in water with high demand for chlorine.

EXAMPLE 4

Efficacy of Oxidizing and Non-Oxidizing Biocides is a Starch Sizing Mixture (Paper Industry)

Efficacy was measured at 60° C.

$NH_4Br+NaOCl$: stock concentration 0.1%.

Dosage: 30 ppm active ingredient.

Incubation temperature 60° C.

TABLE IV

| Biocide | Surviving MOs (cfu/ml) after time (hours) | | | |
|---|---|---|---|---|
| | 4 | 28 | 48 | 72 |
| MBT | $9 \times 10^4$ | $4 \times 10^4$ | $2 \times 10^4$ | $2 \times 10^4$ |
| NaOCl + NaBr | $4 \times 10^3$ | $6 \times 10^5$ | $3 \times 10^5$ | $3 \times 10^6$ |
| NaOCl | $4 \times 10^3$ | $2 \times 10^6$ | $3 \times 10^6$ | $3 \times 10^6$ |
| NaOCl + $NH_4Br$ | $2 \times 10$ | 3 | 0 | 0 |
| MIT | $2 \times 10^4$ | $2 \times 10^3$ | $2 \times 10^3$ | $1 \times 10^3$ |
| DBNPA | $3 \times 10^4$ | $2 \times 10^5$ | $2 \times 10^5$ | $1 \times 10^5$ |
| Control | $1 \times 10^5$ | $3 \times 10^5$ | $8 \times 10^5$ | $7 \times 10^5$ |

Results in Table IV prove that a mixture of $NH_4Br+NaOCl$ is more effective than other oxidizing and non-oxidizing biocides in a high demand medium.

EXAMPLE 5

Kinetics of Kill of Various Mixtures of Ammonium Salts Mixed with NaOCl in Water from a Citrus Juice Evaporator Dosage: 30 ppm as $Cl_2$ Demand: Higher than 30 ppm out of 30 ppm of $Cl_2$ during 10 minutes.

Stock concentration of $NH_4X+NaOCl$: 0.1% as $Cl_2$

TABLE V

| Biocide | residue as $Cl_2$ free (total) after time (minutes) | | | Surviving MOs after time (minutes); total aerobic (total anaerobic) cfu/ml | | |
|---|---|---|---|---|---|---|
| | 10 | 20 | 60 | 10 | 20 | 60 |
| $NH_4Cl$ + NaOCl | 5 (10) | 1 (2) | 0 (0) | $5 \times 10^2$ ($4 \times 10^2$) | $3 \times 10^2$ ($2 \times 10^2$) | $1 \times 10^2$ (3) |
| $NH_4Br$ + NaOCl | 0 (0) | 0 (0) | 0 (0) | $4 \times 10^2$ ($4 \times 10^2$) | $5 \times 10^2$ ($4 \times 10^2$) | $5 \times 10^2$ ($2 \times 10^2$) |
| $NH_4NO_3$ + NaOCl | 6 (9) | — | 0 (0) | $4 \times 10^2$ ($2 \times 10$) | $4 \times 10^2$ (7) | $8 \times 10$ (2) |
| NaOCl | 0 (0) | 0 (0) | 0 (0) | $2 \times 10^5$ ($8 \times 10^4$) | $2 \times 10^7$ ($3 \times 10^6$) | $1 \times 10^7$ ($3 \times 10$) |
| NaOCl + NaBr | 0 (0) | 0 (0) | 0 (0) | $2 \times 10^7$ ($4 \times 10^6$) | $1 \times 10^7$ ($3 \times 10^6$) | $2 \times 10^7$ ($2 \times 10^6$) |
| CONTROL | — | — | — | — | — | $2 \times 10^7$ ($6 \times 10^6$) |

Results in Table V show that mixtures of ammonium salts and NaOCl are effective in controlling aerobic and anaerobic microorganisms in water with high demand for chlorine. Control was achieved within 10 minutes. Under these conditions both NaOCl and NaOBr are impaired by the media. The mixture of $NH_4Br+NaOCl$ did not leave a measurable residue after 10 minutes, yet it was very effective in reducing viable counts within 10 minutes.

EXAMPLE 6

Efficacy of Oxidizing Biocides in Water Taken from a Paper Mill (Thick Stock of Pulp Slurry)

Dose: 15 mg/l as $Cl_2$

Microorganisms were incubated at 37° C. (total aerobic viable counts).

Concentration of stock solution: 0.1% as $Cl_2$.

TABLE VI

| Biocide | Viable counts after time (minutes) cfu/ml | | |
|---|---|---|---|
| | 30 | 70 | 25 hours |
| DBNPA | $2 \times 10^3$ | $6 \times 10$ | $8 \times 10$ |
| NaOCl | $6 \times 10^3$ | $2 \times 10^3$ | $1 \times 10^5$ |
| NaOCl + NaBr | $1 \times 10^4$ | $5 \times 10^3$ | $2 \times 10^6$ |
| $NH_4Br$ + NaOCl | 1 | 0 | 0 |
| CONTROL | $7 \times 10^6$ | — | $1 \times 10^7$ |

Results in Table VI prove higher efficacy for $NH_4Br+NaOCl$ as compared to other oxidizing biocides in this heavily loaded water.

EXAMPLE 7

Efficacy of a Series of Biocides in Domestic Waste Containing a High Concentration of Amines Contact time: 10 minutes Dose: 60 ppm as $Cl_2$ Incubation temperature: 27° C.
Stock concentration: 0.2%
N as $NH_{3;\ 50}$ mg/l; pH: 6.10.

TABLE VII

| Biocide | Residue free (total) as $Cl_2$ after 10 minutes | Surviving MOs (cfu/ml) after 10 minutes | | |
|---|---|---|---|---|
| | | aerob. | anaer. | fungi |
| NaOCl | 0.2 (1.5) | $9 \times 10^2$ | $3 \times 10^3$ | $2 \times 10$ |
| $NH_4Cl$ + NaOCl | 3.0 (9.0) | $2 \times 10^2$ | $4 \times 10^2$ | 0 |
| DBNPA | 0 (0) | $2 \times 10^6$ | $5 \times 10^5$ | 0 |
| Control | — | $5 \times 10^7$ | $1 \times 10^6$ | $2 \times 10$ |

Results in Table VII prove that in the presence of a high $NH_3$ concentration, NaOCl was less effective than pre-mixed $NH_4Cl$+NaOCl in controlling microbial growth (in water with high demand for $Cl_2$); good control was measured after 10 minutes.

EXAMPLE 8
Efficacy of Oxidizing Biocides in Domestic Waste
   Non-treated domestic waste roughly filtered; contact time: 10 minutes.
   Stock concentration: 0.5% as $Cl_2$.
   Dose: 20 ppm as $Cl_2$

TABLE VIII

| treatment | residue as $Cl_2$ ppm free (total) | Fecal coli cfu/ml | total count cfu/ml |
|---|---|---|---|
| NaOCl | 0 (0) | $5 \times 10^5$ | $6 \times 10^6$ |
| NaOCl + NaBr (1:1) | 0 (0) | $3 \times 10^5$ | $7 \times 10^6$ |
| NaOCl + $(NH_4)_2SO_4$ (1:1) | 0.05 (0.7) | $3 \times 10^3$ | $3 \times 10^4$ |
| non-disinfected | | $5 \times 10^5$ | $1 \times 10^7$ |

Results in Table VIII prove that pre-mixing $(NH_4)_2SO_4$ with NaOCl resulted in lower viable counts of both fecal coli and total count.

In waste water with high organic load, this disinfection method was superior to disinfecting with either NaOCl or NaOBr.

EXAMPLE 9
Efficacy of Biocides in the Presence of Anti-Scale and Corrosion Inhibiting Treatment (CWC)
   Stock concentration: 0.5% as $Cl_{12}$
   Efficacy against pseudomonas sp.
   CWC: 100 mg/l
   pH: 9.0
   Contact time: 5 hours

TABLE IX

| treatment | dose mg/l | Survivors in buffer | Survivors in CWC (100 mg/l) |
|---|---|---|---|
| DBNPA | 4 | 0 | $4 \times 10^6$ |
| BCDMH | 4 | 0 | $3 \times 10^5$ |
| $NH_4Br$ + NaOCl | 1 | 0 | $1 \times 10^3$ |
| | 5 | 0 | $2 \times 10$ |

Results in Table IX prove that in the presence of scale and corrosion inhibitors, efficacy of various biocides was impaired to such an extent that much higher dosages of biocides had to be fed in order to maintain good control. The mixture of $NH_4Br$+NaOCl was less impaired by CWC and established good microbial and algal control even in the presence of CWC.

EXAMPLE 10

Pre-mixing Versus in Situ Addition of Ammonium Salts and NaOCl

Water from a corn-processing plant; high demand for $Cl_2$
Dose: 12 ppm
$NH_4Cl$+NaOCl: stock concentration: 1%
$NH_4Br$+NaOCl: stock concentration: 0.5%
Stock solutions were formed at pH 14.0; 7.0, 4.0 and in water.
For in situ addition: both $NH_4X$ and NaOCl were dissolved at the appropriate pH.

TABLE X

| | Survivors cfu/ml (total count after time in minutes) buffer | | | | | | | |
|---|---|---|---|---|---|---|---|---|
| | pH — 14.0 | | pH — 7.0 | | pH — 4.0 | | $H_2O$ | |
| Treatment | 60 | 180 | 60 | 180 | 60 | 180 | 60 | 180 |
| $NH_4Br$ + NaOCl | $1 \times 10^6$ | $8 \times 10^5$ | $2 \times 10^5$ | $1 \times 10^6$ | $1 \times 10^6$ | $1 \times 10^6$ | $6 \times 10^4$ | $1 \times 10^4$ |
| $NH_4Cl$ + NaOCl | $1 \times 10^5$ | $1 \times 10^5$ | $6 \times 10^4$ | $6 \times 10^3$ | $7 \times 10^5$ | $1 \times 10^6$ | $5 \times 10^4$ | $7 \times 10^3$ |
| $NH_4Br$ + NaOCl in situ | $1 \times 10^6$ | $2 \times 10^6$ | — | — | $2 \times 10^6$ | $2 \times 10^6$ | $5 \times 10^6$ | — |
| $NH_4Cl$ + NaOCl in situ | $8 \times 10^5$ | $2 \times 10^5$ | — | — | $1 \times 10^6$ | $1 \times 10^6$ | $2 \times 10^6$ | $2 \times 10^6$ |
| NaOCl | — | — | — | — | — | — | $2 \times 10^6$ | $2 \times 10^6$ |
| NaOCl + NaBr | — | — | — | — | — | — | $3 \times 10^6$ | $3 \times 10^6$ |
| Control | | | | | | | $4 \times 10^6$ | — |

Results in Table X prove that the efficacy exhibited by mixtures of $NH_4X$+NaOCl depend on the pH and on the mode of formation of the stock mixture. In situ addition of the two ingredients to water resulted in lower efficacy at any of the examined pH's.

Stock mixture of $NH_4Br$+NaOCl was more effective when prepared in water than when prepared in buffer at pH 7.0. When the stock solution was prepared at a high or at a low pH, it was less effective.

EXAMPLE 11
Dependence of Efficacy of Mixtures of NH$_4$Br+NaOCl on the Concentrations of Stock Solution Work was carried out in industrial waste water.

Stock concentrates were prepared in buffer at pH 7.00.

Biocidal dose: 4 ppm as Cl$_2$.

TABLE XI

| treatment | Survivors cfu/ml total count after time (minutes) | | |
|---|---|---|---|
| NH$_4$Br + NaOCl | 10 | 60 | 180 |
| 2% | 6 × 10$^4$ | 1 × 10$^4$ | 2 × 10$^3$ |
| 1% | 2 × 10$^5$ | 3 × 10$^4$ | 3 × 10$^4$ |
| 0.5% | 7 × 10$^4$ | 2 × 10$^4$ | 4 × 10$^3$ |
| 0.01% | 2 × 10$^6$ | — | 2 × 10$^6$ |
| in situ | 5 × 10$^5$ | 3 × 10$^5$ | 5 × 10$^5$ |
| NaOCl | 9 × 10$^5$ | — | 7 × 10$^5$ |
| Control | 1 × 10$^6$ | — | — |

Results in Table XI prove that the efficacy exhibited by the mixtures correlated with the concentration of stock solutions. The highest efficacy was measured with a stock concentration equal to at 0.5% as Cl$_{12}$. Similar trends were obtained when the stock solutions were prepared in water rather than in buffer (see Table X) (The high efficacy measured in buffer at a level of 2% as Cl$_2$ results from the higher pH of this mixture.)

Field Experiments

Example I

Cooling Tower 1
  contained volume 1000 m$^3$
  Circulation rate 500 m$^3$/h
  Scale and corrosion inhibitor: CWC: 100 mg/l The tower was controlled on low level (0.6–1.2 kg/day) of BCDMH feed. Use of BCDMH was effective as long as make-ups were softened in ion-exchangers.

When CWC (100 mg/l of phosphonate) replaced the use of ion-exchangers, much higher dosages of BCDMH (4–5 kg/day) did not suffice to prevent biofouling and growth of algae.

The system was shock-fed with NH$_4$Br+NaOCl. Overall dosage: 75 liters NaOCl (10%) 12.6 kg NH$_4$Br: The mixture was fed during 1.5 hours. This shock treatment cleaned the system.

A slug dose of 25 liters NaOCl (10% as Cl$_2$) (+4.2 kg NH$_4$Br) was then fed to the cooling tower once in two to three days. The cooling tower remained clean, with no apparent growth of biofilm or algae. A measurable residue of 0.6–0.4 ppm (as total chlorine) was measured in the water 24 and 48 hours after feeding the mixture.

Example II

Cooling Tower 2
  Corn processing plant.
  Contained volume: 20 m$^3$
  Circulation rate: 300 m$^3$/h
  pH: 7.5–8.0
  Water temperature: 36° C.–57° C.

This tower was treated with BCDMH (1.50–2.26 kg/day) daily. Due to a very high organic load in the water, growth of biofilm was very fast. Treatment with BCDMH was effective in controlling the daily grown films, but was not effective against heavy slimes which covered the cooling tower.

A daily feed of 3 liters NaOCl (7% as Cl$_2$), mixed with 0.35 kg NH$_4$Br controlled the daily newly formed biofilm as well as the slime and algae growth covering the cooling tower, and left a clean cooling system after three weeks of daily treatment avoiding the need for shock treatment.

Example III

Starch Sizing Mixture
  Paper mill, starch sizing
  Contained volume: 20 m$^3$
  Flow rate: 8.33 m$^3$/h. (6% starch in H$_2$O),
  pH about 8.0
  Temperature: 50° C.–70° C.

Sizing mixture is recirculated in a size press through a filter (80 microns). Circulation rate: 6 m$^3$/h. The sizing mixture had been previously treated with NaOCl (10% as Cl$_2$), which was fed every 8 hours (30 liters per portion). With this treatment, filters had to be washed once every two hours.

Use of NaOCl was replaced by the use of a mixture of NH$_4$Br+NaOCl (stock concentration 0.5% as Cl$_{12}$).

Feeding of NaOCl (13 liters of 10% as Cl$_2$) and NH$_4$Br (2.5 kg) three times a day (every eight hours) kept the filters in the size press clean; the treatment with NH$_4$Br+NaOCl was compatible with a blue dye added to the sizing mixture, and did not bleach the blue starch, unlike NaOCl.

A number of embodiments of the invention have been described for purposes of illustration, but it will be understood that they are not limitative and that the invention can be carried out by persons skilled in the art with many modifications, variations and adaptations, without departing from its spirit and from the scope of the appended claims.

What is claimed is:

1. A process for killing microorganisms and controlling biofouling in high chlorine demand water, which comprises mixing sodium hypochlorite and ammonium bromide, in a molar ratio calculated as N/Cl of at least 1:1, the concentration of the mixture being 0.01% to 1.0% as Cl$_2$, and immediately adding the resulting mixture to said water.

2. Process according to claim 1, wherein the water has a chlorine demand of at least 1.8 ppm out of 2.0 ppm Cl$_2$ after 60 minutes.

3. Process according to claim 1, wherein the mixture is added to the water at a daily level of at least 2 mg/l as Cl$_2$.

4. Process according to claim 26, wherein the temperature of the mixture is 10–30° C.

5. Process according to claim 1, wherein the sodium hypochlorite and the ammonium bromide are mixed and the mixture is fed continuously to the water to be treated.

6. A process according to claim 1, wherein the concentration of the sodium hypochlorite/ammonium bromide mixture is from 0.1% to 0.5% Cl$_2$.

7. A process according to claim 1 wherein the sodium hypochlorite is added to a solution of ammonium bromide.

8. A process according to claim 7 wherein the sodium hypochlorite is added to a well-mixed solution of the ammonium bromide in the range of 0.1% to 1%, until the full concentration of chlorine in the mixture has reached 0.1–1%.

* * * * *

UNITED STATES PATENT AND TRADEMARK OFFICE
CERTIFICATE OF CORRECTION

PATENT NO. : 6,478,973 B1  Page 1 of 1
DATED : November 12, 2002
INVENTOR(S) : Barak It is certified that error appears in the above-identified patent and that said Letters Patent is hereby corrected as shown below:

<u>Title page</u>,
Item [73], Assignee, should read as follows:

-- [73] Assignee: Bromine Compounds Limited, Beer-Sheva (IL) --.

Signed and Sealed this

Twelfth Day of October, 2004

JON W. DUDAS
*Director of the United States Patent and Trademark Office*